(12) United States Patent
Tapper

(10) Patent No.: US 6,485,437 B1
(45) Date of Patent: Nov. 26, 2002

(54) SENSOR CONTROLLED ANALYSIS AND THERAPEUTIC DELIVERY SYSTEM

(76) Inventor: Robert Tapper, 1935 Armcost Ave., Los Angeles, CA (US) 90025

(*) Notice: Subject to any disclaimer, the term of this patent is extended or adjusted under 35 U.S.C. 154(b) by 0 days.

(21) Appl. No.: 09/522,522

(22) Filed: Mar. 10, 2000

Related U.S. Application Data

(62) Division of application No. 09/028,832, filed on Feb. 24, 1998, now Pat. No. 6,059,736.
(51) Int. Cl.[7] ................................................. A61B 5/00
(52) U.S. Cl. .......................................... 600/573; 604/20
(58) Field of Search ................................ 600/573, 584; 604/20, 21, 501; 607/115

(56) References Cited

U.S. PATENT DOCUMENTS

| | | | | |
|---|---|---|---|---|
| 4,822,334 A | * | 4/1989 | Tapper | 604/20 |
| 5,224,927 A | * | 7/1993 | Tapper | 604/20 |
| 6,059,736 A | * | 5/2000 | Tapper | 600/573 |

* cited by examiner

Primary Examiner—Max Hindenburg
(74) Attorney, Agent, or Firm—Fulwider Patton Lee & Utecht, LLP

(57) ABSTRACT

A method and apparatus for non-invasively withdrawing and accurately evaluating analytes quickly, painlessly and reliably from a biological subject automatically and controlling subsequent administration of therapeutic agents in response to such analyte sample analysis. Improvements are provided in electro-osmotic sample withdrawal, dosimetry and iontophoretic delivery subsystems, biosensors electrode construction and arrangement, intervenors, mediators, bolus delivery, and related subsystems.

42 Claims, 8 Drawing Sheets

SENSOR CONTROLLED ANALYSIS AND THERAPEUTIC DELIVERY SYSTEM

This application is a divisional of U.S. patent application Ser. No. 09/028,832 filed Feb. 24, 1998, now U.S. Pat. No. 6,059,736.

BACKGROUND OF THE INVENTION

1. Field of the Invention

This invention relates generally to a new and improved system for sampling and analysis of body fluids and the like, and may also include delivery of therapeutic agents in response to such analysis. More particularly, the invention relates to new and improved methods and apparatus for non-invasively withdrawing analytes from a biological subject automatically and controlling subsequent administration of therapeutic agents.

2. Description of the Related Art

Diagnosis for many human ills is dependent on evaluation of invasive samples of body fluids taken for assay. This invasive procedure is accomplished by withdrawal of the analyte or sample through a needle or the like, with consequent exposure of the patient to injury, possible infection and discomfort. The procedure invariably involves medical professionals that add to the cost of the procedure, e.g. an office visit.

Advances have recently been made in the biosensor field that enable diabetics, for instance, to self-test through the convenience of kits such as the ExacTech® device disclosed in U.S. Pat. Nos. 4,545,382 & 4,711,245. Such a device, while performing a valuable service and representing a quantum leap over professional intervention, is however, still invasive and subjects the patient to the same risks through multiple pin pricks and the like.

One approach to overcoming the aforementioned major shortcomings of invasive procedures is by noninvasive electro-osmotic analyte withdrawal through the unbroken skin or mucosal membrane. Electro-osmosis, sometimes referred to as cataphoresis and/or reverse iontophoresis, was recognized before 1941 by Nernst who showed that urea and sugar can be electrically transported out of the unbroken skin. An extensive bibliography exists on this basic phenomena.

A recent effort by Guy, et al., e.g. as described in U.S. Pat. Nos. 5,279,543 and 5,362,307, attempts to use this basic electro-osmosis technology to extract glucose. However, these attempts fall short of practical success because the proposed technology cannot perform the desired withdrawal procedure within a time span of less than ten minutes, as medically needed so that a glucose measurement would be followed in a timely manner after determination of the appropriate therapeutic insulin level. In this regard, continuously rapid changes of glucose levels, which commonly occurs, require different therapeutic insulin levels. Such limiting constraints on faster performance of sample withdrawal by the prior art is due to the restricted levels of current, voltage and time duration for the device to extract a sample and yet prevent skin injury. Accordingly, the prior art systems offer nothing new in basic electro-osmosis technology to prevent skin injury. Moreover, there is no subsequent controlled automatic delivery of an appropriate therapeutic agent in response to such rapid sample withdrawal and analysis.

Further difficulties have been encountered in achieving satisfactory dosimetry control for iontophoretic administration systems.

Hence, those concerned with the development and use of analyte withdrawal and evaluation systems have long recognized the need for very rapid, painless, accurate, non-invasive analyte withdrawal and analysis and subsequent controlled automatic delivery of therapeutic agents in response to such analysis. The present invention clearly fulfills all these needs.

SUMMARY OF THE INVENTION

Briefly, and in general terms, the present invention provides a new and improved system for sampling and analysis of body fluids, e.g., analytes, and delivery of therapeutic agents in response to such analysis and, more particularly, to improvements in methods and apparatus for non-invasively withdrawing and accurately evaluating analytes quickly, painlessly and reliably from a biological subject automatically and controlling subsequent administration of therapeutic agents in response to such analyte sample analysis.

By way of example, and not necessarily by way of limitation, the present invention provides a system wherein limits of low electrical voltage and current previously imposed on prior art systems to prevent skin injury, are now overcome through unique electrical circuitry and long tunnel physical routing of applied electrical voltage, thereby achieving high sampling current density. This facilitates rapid sampling which can be completed well under 10 minutes. In this regard, the process of the present invention enables use of 60 volts or more producing a controlled sampling current for complete comfort, and provides an analyte reading in 15 seconds or less.

In accordance with the invention, the aforedescribed features are accomplished, in part, by providing a long tortuous path between the applied high voltage and the skin of a biological subject. This path between the voltage source and the skin typically consists of a solvent or water wetted wool as an intervenor. Since the injury is caused by sodium hydroxide (lye) migrating from the negative voltage source electrode, the wool (or composite) acts as a barrier to the rather large sodium hydroxide molecule to prevent injury within the 10 minute treatment period.

Since one aspect of the invention involves a diagnostic tool, accuracy and repeatability are paramount. To achieve this, the invention provides that the current and time used to obtain the analyte sample be integrated and interdependent on each other, so that the identical quantitative sampling is always obtained. In this way, the identical amount of analyte is always withdrawn as a sample, despite the substantial variabilities of skin resistance on an individual.

Another aspect that limits the use of higher electrical currents is the pain involved. Usually, both electrical polarities are in direct contact with the skin through a felt or gel intervenor. Of the two polarities, the sensation at the positive electrode is typically far more painful. If therefore, direct contact of the positive electrode is removed from the skin, it allows a large increase in sampling current without the discomfort normally associated with such electrical currents and while still obtaining the analyte such as glucose at the negative electrode.

To eliminate pain caused by the positive polarity at high currents, additional novel technology is provided in accordance with the invention. Previously used circuitry in iontophoresis used both electrical polarities applied to the skin surface to "complete" or ground the circuit. In the practice of the present invention, the negative polarity is chosen to sample an analyte such as glucose and the positive electrode is no longer directly connected to the body as a ground return but stays within the device housing with its dropping resistor connected to the skin (ground) to complete the circuit. This ground is essentially neutral electrically. The negative polarity is in electrical contact with the skin through the aforedescribed wetted, long wool intervenor and then through a wetted membrane on the skin which acts as a collector for the analyte. Of course, for other applications these polarities could be reversed and, again, only a single electrical polarity is in contact with the skin.

The present invention also provides a system to assay or measure the sample. A pair of electrodes are provided facing each other with analyte selective enzyme coated on one electrode, e.g., the working electrode, or, alternatively, on the membrane facing the working electrode. A bi-layer membrane is inserted between these electrodes and serves the purpose of connecting directly to the skin on one end while the other end is in contact with the long narrow intervenor that is connected to the high voltage negative source. When wetted with an electrolyte of pH 7.4, a continuous circuit is provided from this high voltage source to the skin (with felt pad and membrane in between). Thus, in accordance with the invention, a "sandwiched" bi-layer membrane in between an enzyme coated electrode(s) or membrane is provided as a mechanical structure to extract the analyte sample and convey it to any appropriate digital readout subsystem.

The biosensor circuit is separate from the withdrawal circuit and comes into play after the analyte sample has been withdrawn. The dosimetry circuit turns the device on for the predetermined setting of less than 15 ma./sec., for example, to extract the analyte. Upon completion of this cycle, the readout subsystem is activated and provides a reading on its digital display. Of course, any number of detection systems are available and would be suitable for the readout subsystem, including those in the public domain.

In accordance with the invention, electronically produced gases serving as a mediator are generated at the high voltage negative terminal. The negative polarity, besides producing the necessary current to withdraw the analyte, also produces hydrogen gas at the negative pole which migrates towards the positive pole and thus passes through the membrane and between the biosensor electrodes. The hydrogen gas is a reduction agent and reduction cannot exist without oxidation. This oxidizes the immobilized enzymes on the electrodes/membrane and the captured glucose analyte. This also causes electron transfer to the electrodes that is proportionate to the concentration of analyte.

Hydrogen gas is an excellent redox species and is far superior to the "one shot" mediator of prior art devices, such as that utilized in the well-known and commercially available ExacTech® system, because it comes from a renewable source. This process also produces the halogen chlorine which further aids in oxidation.

In addition, in accordance with the invention, the high voltage source is dosimetry controlled and, therefore, not only quantitatively controls the analyte withdrawal, but also controls the quantity of the aforementioned hydrogen/chlorine gas mediator which is generated.

This negative electrode generated hydrogen also serves other important functions. Since hydrogen has a special affinity for palladium and will permeate its surface, this may be used to advantage by providing a sensor electrode of palladium. Hydrogen interacts with the palladium to lower resistance. If the working electrode is palladium and the second electrode is of the hydrogen resistive alloy NASA-23 or its equivalent, the resistance or work function between both electrodes is lowered. Because the NASA-23 or equivalent electrode is impervious to the hydrogen gas, it serves as an excellent reference electrode relative to the palladium electrode.

Still other benefits accrue when hydrogen ions combine with the solvent water molecules to create hydronium ions. The hydronium ions are crucial to the cellular processes which lead to enzyme catalysis and membrane transport.

In accordance with the invention, very high potentials (over 1v.) are provided to cause the redox reaction. There is a two-step process, i.e., 1) a high voltage to cause the redox (generated by the reducing agent hydrogen), and 2) then revert to an extremely small voltage (under 1v.) to activate the transducer and readout system. This occurs almost instantaneously because the conventional time of 20–30 seconds to await the redox reaction has already taken place in much less time by the high voltage caused hydrogen that led to that event in shorter time than any prior art device.

Accordingly, and in view of the foregoing, the process of the present invention includes application of a large negative voltage to a small area of the skin to cause the electro-osmotic withdrawal of body fluids. This same high voltage has another attribute in that it generates hydrogen—the same hydrogen gas that will lead to the oxidation of the glucose enzyme(s) that separates out the glucose analyte from interferents. This causes the cycle of events that will result in electron transfer from the closely associated enzyme(s) coated electrodes or membranes to provide a measure of glucose concentration. Moreover, the source for the hydrogen is unlimited and repeatable, therefore making the process available on demand without the physical presence of any consumable chemical mediators. Since the enzymes are reusable, the economy and simplicity of operation of such a device provides clear advantages to the patient.

To reuse the device and obtain new glucose measurements and repeat the events leading to insulin infusion, known as recovery time, the second half of the one cycle long signal may (optionally) reverse polarity and return the system to neutral. Alternatively, one just has to wait several minutes for the hydrogen to dissipate, and the entire process can then be repeated.

Another feature of the present invention that improves the minute sampling taken through the unbroken skin is the use of the amplification or regeneration capability of certain chemical combinations. If the electrodes are coated with coupled enzymes, such as glucose oxidase or glucose dehydrogenase in the presence of cofactors NAD/NADH and HADPH or NADH, then the extremely minute analyte coming through the skin is "ping ponged" between competitive enzymes and, therefore, multiplied. Another benefit of this is improved separation between the target glucose and interferents.

Hence, various aspects of the present invention facilitate noninvasively withdrawing body fluid and provide novel sensor technology to create a mediator and to control the quantity of this mediator for accurately determining analyte concentration for diagnostic purposes. These inventive features can be used separately or in combination and they both use common components that have multiple functions. This dual capability of noninvasive sampling and controlling the target inorganic or organic substance is a linchpin to the control and operation of a therapeutic drug delivery unit such as that described in U.S. Pat. No. 5,224,927 by the same inventor, Robert Tapper, as the present invention. This "closed loop" arrangement provides for self-regulated insulin infusion controlled by the monitored glucose reading using the biosensor described above. The entire device can fit into an externally worn, topically applied "patch".

Another important feature referred to in U.S. Pat. No. 5,224,927 is the ability of this device to adjust the pH of the drug delivery reservoirs and/or a biosensor skin contact membrane (known as BLM or s-BLM). The pH adjustment range is approximately 4 to 8 and can aid in permeability for both infusion of drug or increasing withdrawal of analyte. For instance, in view of the nonconductive wetted collection bi-layer membrane (BLM) in contact with the skin, and in view of the poorly conductive insulin in the drug delivery chambers, optimal performance would take place if the solution were adjusted to the appropriate pH. An important function of the s-BLM membrane is that it can be used as a pH probe for pH measurement. The resulting pH data is then the basis for any suitable pH control circuit to adjust pH as needed.

The aforedescribed system of the present invention relates in particular, and only by way of example, to the needs of a diabetic. Another need of the diabetic is that they be given a "bolus" shot of insulin at mealtime. A bolus shot requires the infusion of a large dose of insulin compared to the patient's baseline maintenance level of insulin. The system described in U.S. Pat. No. 5,224,927 is readily adapted to meet this demand for an extra large dose in the following manner.

By activating a designated electrical bolus switch, both drug delivery reservoirs of the patch are made active simultaneously instead of their normal operating mode of sequential drug delivery (due to the very slow A.C. operating signal). Since the bolus switch causes both reservoirs to deliver insulin simultaneously by giving them the identical negative polarity, the dosage is thereby doubled over baseline.

As previously indicated, the positive polarity stays within the electronic patch housing and is connected to the skin through a dropping resistor. The skin or ground is relatively neutral at this point. This feature lifts the positive polarity off the skin, thereby eliminating the more painful and non-contributing polarity from skin contact. This, in turn, allows the patient to at least double the electrical current setting, thereby again doubling dosage for a total of four times over maintenance level for short term delivery. For this short term delivery a D.C. signal is used. Because it is a D.C. signal, skin injury could be expected unless corrective action were taken. Until now, the use of the pH control circuit served the singular purpose of optimizing permeability and, therefore, delivery by making the solvent compatible with the drug of choice and its polarity.

In accordance with the invention, pH control is also used to prevent skin injury when using D.C. for the short term. For instance, in the example cited above, the negative polarity was used to drive insulin from both reservoirs. The injurious sodium hydroxide generated at the negative pole must then be offset. This can be done by pretreating with the positive polarity, thereby building an acidic reserve pH of approximately 4 (by way of example) in the drug delivery reservoirs. Drug delivery is then activated with a negative polarity driving the pretreatment pH up toward the alkaline state. Before the reservoirs reach pH 8, the delivery signal must be stopped for another short dosage of pH 4 caused by the positive polarity. Thus, in the practice of the present invention, injury is prevented by avoiding extremes of pH as measured by the s-BLM probe.

The present invention also includes a unique electrode system that allows current to be elevated at least 200% over present levels. A pair of large drug delivery electrodes is provided. In accordance with the invention, another pair of ancillary electrodes are added on the outside perimeter of the drug delivery electrodes. These ancillary electrodes also cross between and are insulated from the drug delivery electrodes. The outer ancillary electrodes are also typically driven at a frequency of approximately one cycle per minute. This is the second harmonic of the basic drug delivery generator whose frequency is approximately one cycle every two minutes. It has also been discovered that the use of sodium salicylate instead of tap water with these ancillary electrodes is able to further mask the pain sensation arising from the drug delivery electrodes, so as to facilitate additional large increases in the drug delivery electrical current levels.

Another important need for a bolus shot is in the field of anesthesia since it is desirable for quick action to alleviate pain. The same procedure for elevated infusion applies as described above with pH control to avoid injury, but may require switching polarities since many analgesics are positive. In this regard, and by way of example, a D.C. signal is used with novel circuitry to obtain greatly elevated drug delivery levels without skin injury or pain. To lessen pain and skin injury from the positive reservoirs, these electrodes are connected through a dropping resistor, instead of connecting them directly to the positive terminal of the voltage supply. This causes a large drop across the resistor and makes the electrode relatively less positive than the source voltage. Electrical current still flows because the negative polarity is directly connected to the skin through the wetted pad. This provides a lifting and isolation of the pain-causing high positive voltage relative to the skin, and also allows increased electrical current and therefore faster therapy. Diminished positive voltage at the skin also decreases the potential for irritation from this contact. Importantly, it has been discovered that adding sodium salicylate to the negative pad also diminishes skin injury which would be a concern with a D.C. device.

The aforedescribed artificial pancreas of the present invention has obvious advantages over present day invasive systems that include expensive and risky implants.

It is to be understood that the noninvasive biosensor described above used glucose as the target analyte only as an example and not by way of limitation. For instance, there are hundreds of different dehydrogenases and several thousand enzymes. Besides glucose analysis, important diagnostic applications could include, again by way of example only, urea, creatinine, lactate, cholesterol, aspirin and paracetamol, among others. In addition, noninvasive sample analysis may be made of body fluids to compare then to normal levels or to track administered drug levels.

Since the present invention focuses on a means of determining the concentration of chemical or body fluid components to assess a condition, another important application is facilitated. During iontophoretic drug delivery, it has long been an enigma to determine what portion of the reservoir drug has been infused. In this regard, the same means of determining concentration with the biosensor described above may be applied to assessing the drug remnant in a drug infusing device, therefore assuring the user of adequate drug availability, etc. This occurs because a decrease of concentration indicates percutaneous absorption into the body of the solute or drug. This information may also be important to the investigator during the testing of a new drug, for quantitative analysis of drug related to an effect. The present invention thus nominally replicates the extremely expensive HPLC lab instrument at a fraction of the cost.

Still another important application in accordance with the invention, comes about as a result of this ability to assess drug concentration in an iontophoretic drug delivery reservoir. It has always been a problem to have an adequate supply of drug available in the drug reservoir for long term, continuous delivery. It is not practical to make an overly large patch because it must be worn and would meet patient objection. Moreover, the literature places concentration restrictions on iontophoretic drug delivery to 2% solutions, claiming reduced flow above this point because of ionic clutter. In accordance with the present invention, a novel way of eliminating this problem and allowing delivery over time with a relatively small patch is to provide a reserve reservoir that contains a concentrate of the desired drug in aqueous solution. This concentrate is considerably over 2%—perhaps 20 or 50%. Upon receiving information from the drug delivery reservoir that the concentration is less than the initial filling of 2%, the biosensor triggers the reserve reservoir to release enough of the concentrate to make up the difference that was infused. In this manner, the drug delivery reservoir is continuously replenished.

The structure of the reserve reservoir is a separate compartment for the concentrate with a membrane covered opening. The membrane has a voltage across it with selective polarities to act as a valve to open or shut off the flow of concentrate as needed. This action may be enhanced with an ion exchange membrane. The solvent is replenished automatically by virtue of the fact that an A.C. signal is used. This causes the hydrogen and hydroxide ions to migrate together to form water.

Various other embellishments known in the art can be practiced in this invention. They include immobilization of the enzyme biocomponent and restriction of the flow of analyte diffusion. The best biosensor design is to build a "direct" device with biocomponents immobilized directly on the transducer. Other characteristics of construction include the close proximity of the biological and physicochemical components to each other to improve efficiency.

The present invention also provides in combination with the aforedescribed sample withdrawal and assay, and in response to electrical input from the assay subsystem, a new and improved method and apparatus for applying electrical energy topically to a suitable surface of a biological subject, such as the skin of a human body, particularly for the long term administration of medicaments and the like or for other electrotherapeutic treatment, and by which the aforementioned deficiencies and undesired side effects are greatly minimized and may be eliminated.

Moreover, the system of the present invention is relatively inexpensive to manufacture, can be physically packaged in a completely self-contained, relatively simple and compact configuration, is trouble free and reliable in use, is capable of higher drug administration rates and drug concentrations, can deliver multiple drugs simultaneously in a simple manner, can control pH at the delivery site, is capable of delivering large and/or heavy molecule drugs, is a more effective bactericidal, and is arranged to be safely, simply and reliably operated for self-treatment by an average person in normal home use, even for extended periods of several days at a time to unlimited use for the chronically ill patient. Furthermore, it is contemplated in the practice of the invention that electrical impedance at the administration site on the patient can be substantially reduced to vastly improve permeability and penetration and thereby further enhance medicament delivery.

In this regard, the present invention is directed to the combination of a new and improved system for ionto- phoretic drug administration, in response to an assay measurement signal, which includes conducting direct electrical current through the skin of a body, and periodically reversing the electrical current and conducting the current through the skin in the opposite direction, to effectively deliver very low frequency A.C. current, substantially in the critical range of approximately 0.0027 Hz to 10 Hz. It has been discovered (see U.S. Pat. No. 5,224,927) that, within this substantially critical frequency window between approximately six minutes per full cycle and approximately ten cycles per second, a dramatic cancellation of skin damaging ions takes place. At frequencies higher than approximately 10 Hz, no substantial effective delivery takes place. At frequencies lower than approximately 0.0027 Hz, the risk of skin injury increases substantially.

As previously indicated, it is well known that the positive iontophoretic electrode, in addition to its primary function of driving like polarity ionic substances into the skin of a subject, unfortunately produces skin damaging hydrochloric acid as well. Likewise, the negative iontophoretic electrode, in addition to its primary function of driving like polarity ionic substances into the skin, unfortunately also produces skin damaging sodium hydroxide. However, within the aforestated frequency range of the present invention, either driving polarity delivers the desired ionic therapeutic substances, but also cancels the undesired skin damaging ions with the reverse portion of the electrical cycle. The reason for neutralization of the harsh injury producing chemicals, i.e., hydrochloric acid and sodium hydroxide, is that both of these chemicals require a finite period of time on the skin to cause damage. Hence, these damaging chemicals are made to cancel each other before damage takes place, by critical frequency selection, in accordance with the invention, of the A.C. driving signal. Therefore, optimization of a long sought therapeutic device with reduced side effects has been achieved.

In this regard, electronic circuitry is provided to automatically impose the reversal of electrical current at regularly repeating intervals of time, in accordance with the aforedescribed substantially critical frequency range, and the system can be adjusted to conduct the iontophoretic treatment at any desired level of electrical current, such treatment being under the control of the previously described sample withdrawal and assay subsystem.

The present invention also provides, as previously indicated, a method and apparatus for electrical dosimetry control in the application of electric currents to withdrawal of analyte samples, dosimetry in sample withdrawal being determined automatically by the product of time and administered electrical current. In this regard, the present invention is directed to a system for electrical dosimetry measurement and control, wherein the product of administered electrical current and time for total dosage is maintained constant, while either variable, time or electrical current magnitude, may be changing.

By way of example and not necessarily by way of limitation, the system includes means for automatically establishing the magnitude of the desired total sample withdrawal dosage in terms of delivered time-current product and means for sensing the magnitude of the electrical current and converting that magnitude to a voltage for varying the frequency of a voltage controlled oscillator as a function of the electrical current magnitude. Means are also provided for measuring and accumulating the electrical output of the oscillator over time, in a suitable counting device, as an indication of the actually delivered time-current product. In addition, means are provided for comparing the delivered time-current product registered in the counter, as a running measure of withdrawn sample dosimetry during the sampling procedure, with the desired total dosage previously established, so that the application of the sample withdrawing electrical current will be terminated when the time-current product actually administered equals the desired total withdrawal dosage.

The new and improved electrical dosimetry control system of the present invention for sample withdrawal is extremely accurate, reliable and easy to use. The system provides enhanced patient comfort and high precision in automatically establishing administered electrical current dosage for consistent sample withdrawal.

Hence, the present invention provides a new and improved method and apparatus for very rapid, painless accurate, non-invasive analyte withdrawal and analysis and subsequent controlled automatic delivery of therapeutic agents in response to such analysis. The invention also provides new and improved subsystems and components for enhancing the practice of the invention.

These and other objects and advantages of the invention will become apparent from the following more detailed description, when taken in conjunction with the accompanying drawings of illustrative embodiments.

DETAILED DESCRIPTION OF THE PREFERRED EMBODIMENTS

Figure 1:
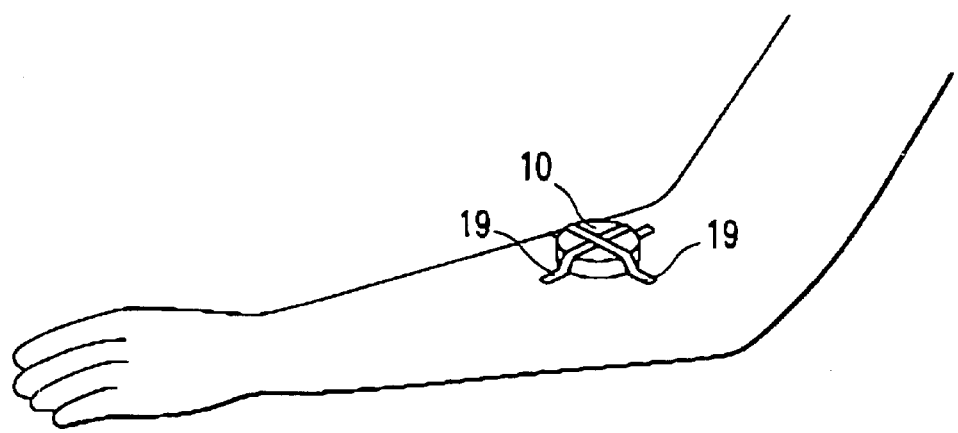
FIG. 1 illustrates an iontophoretic patch sample withdrawal, evaluation and administration device constructed in accordance with the invention, and shown installed upon the arm of a human subject.

Referring now to the drawings, like reference numerals denote like or corresponding parts throughout the drawing figures.

As best observed in FIG. 1, there is shown a combined electro-osmotic analyte withdrawal, evaluation and iontophoretic patch administration device 10, of relatively simple, economical, reliable and compact construction, embodying features of the present invention. The patch 10 is shown installed upon the arm of a suitable biological subject so that the patch contacts the skin 11 of the subject for appropriate analyte withdrawal, assay and subsequent administration of therapeutic treatment by iontophoretic delivery of medicaments or the like. By way of example, the patch 10 is held in position by a pair of tapes 19.

While the device 10 is shown in its presently preferred embodiment as a compact patch, it will be appreciated by those of ordinary skill in the art that a larger structural and/or physical packaging unit (not shown) may be utilized and also embody various features of the present invention.

The structural details of the portion of the patch 10 and the administration system relating to iontophoretic treatment are set forth in U.S. Pat. No. 5,224,927, issued Jun. 6, 1993, inventor Robert Tapper, the same inventor as the present invention, and all of the disclosure of that patent is specifically incorporated by reference in this specification as if set out completely herein.

Figure 2:
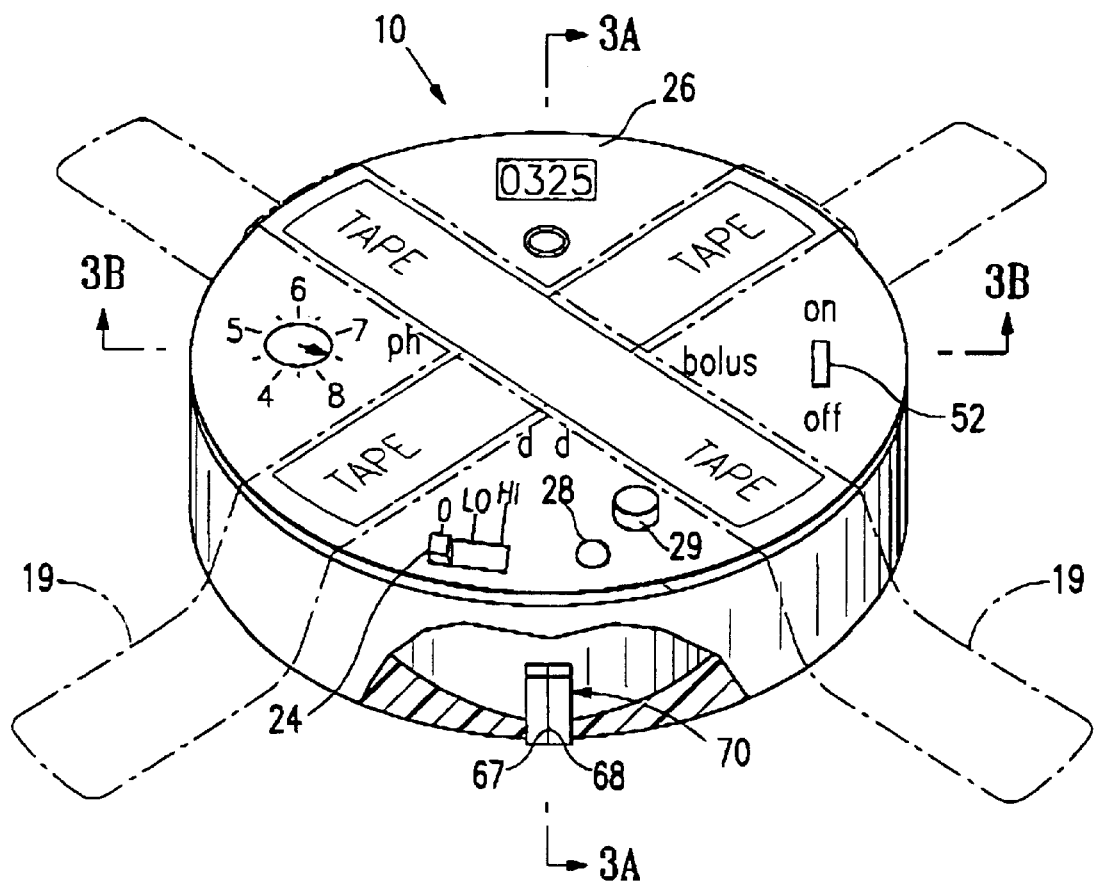
FIG. 2 is an enlarged, perspective view of a presently preferred embodiment of a patch constructed in accordance with the invention, portions being broken away to illustrate internal structure.
Figure 3A:
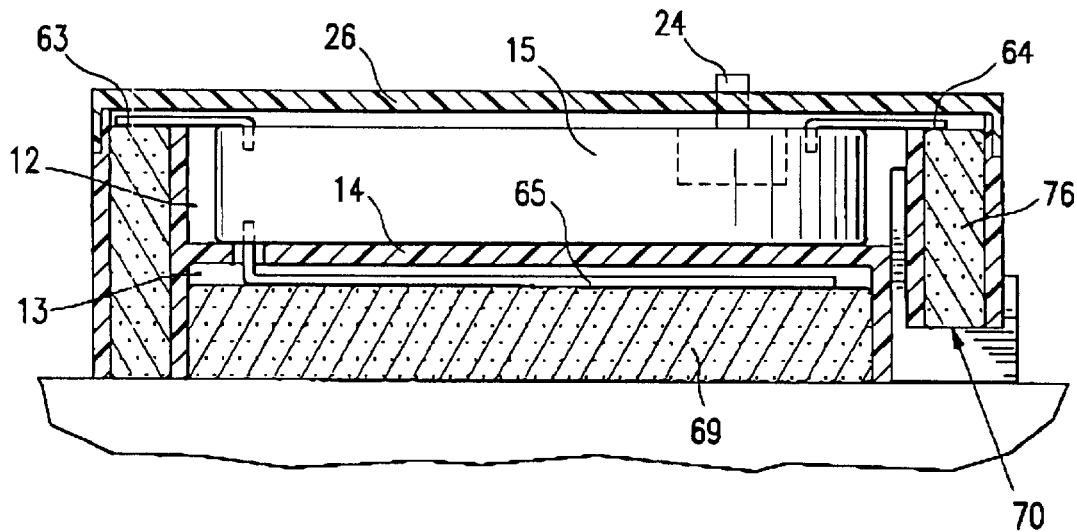
FIG. 3A is a sectional view, taken substantially along the line 3A—3A in FIG. 2.
Figure 3B:
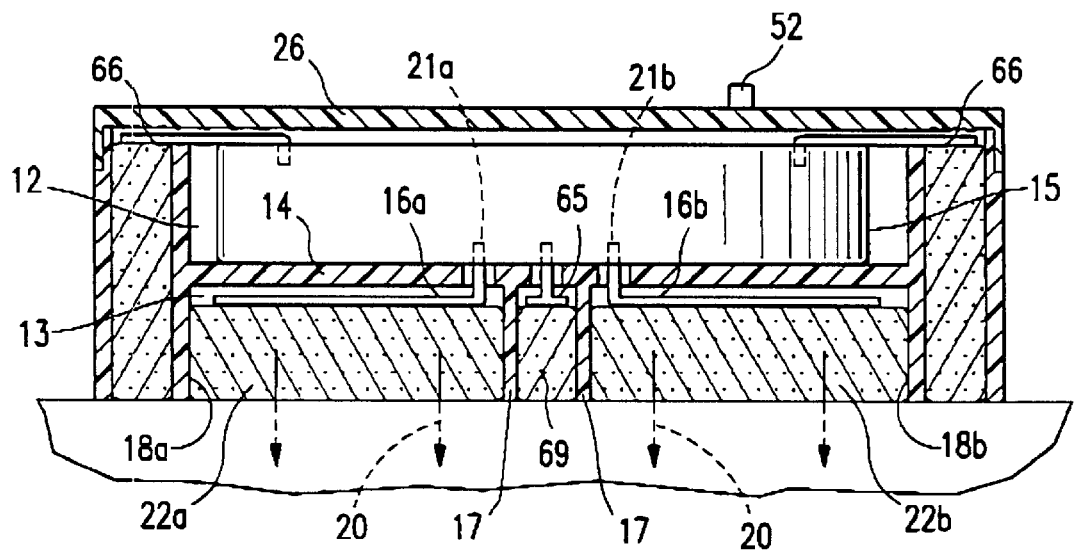
FIG. 3B is a sectional view, taken substantially along the line 3B—3B in FIG. 2.

As best observed in FIGS. 2, 3A and 3B of the drawings, the iontophoretic patch 10 is a very compact, circular, cylindrical device fabricated primarily of an outer plastic shell with internal, preferably integrally molded, baffles. The plastic shell and baffles are typically molded of an electrically insulating, flexible vinyl material or the like.

The internal baffles divide the interior of the iontophoretic patch 10 into upper and lower, hollow internal chambers 12 and 13, respectively, more specifically, by means of an interior baffle member 14. The upper chamber 12 contains a compact electronics package 15, including a suitable microchip and battery power supply. This upper chamber 12 is electrically insulated from the lower chamber 13 by the plastic baffle member 14.

The lower chamber 13 contains a pair of iontophoretic electrodes, 16a and 16b, typically of electrically conductive silicone/carbon material, and which are separated from each other by a pair of electrically non-conductive plastic divider baffles 17 forming separator walls which divides the lower compartment 13 into a pair of semi-circular electrode chambers and reservoirs 18a and 18b and a narrow chamber for an electrode to be described subsequently herein. The chambers 18a and 18b house the electrodes 16a, 16b and contain the therapeutic substances to be ultimately infused into the biological subject, the drug infusion path being indicated generally by the arrows 20 in FIG. 3B.

The iontophoretic delivery electrodes 16a, 16b are suitably connected electrically into the electronics package 15 via electrically conductive tabs 21a and 21b, respectively, extending through appropriate slotted openings in the chamber dividing baffle member 14. The silicone/carbon electrodes 16a, 16b are typically fabricated of 1–2 ohm per square centimeter conductive plastic material. While the electrodes 16a, 16b are preferably of silicone/carbon in a presently preferred embodiment of the invention, they may be fabricated of other electrically conductive, non-corrosive materials as well. With the A.C. delivery signal used in the system of the present invention, there is little or no resistance buildup in the silicone/carbon electrodes.

The drug reservoirs 18a and 18b are filled either with a gel containing the therapeutic substances to be administered or a pair of felt pads 22a and 22b which have been appropriately saturated with the substances to be dispensed.

In addition, for manual operation, an electrical slide switch 24, allowing selection of dosage, schedule and treatment duration, projects physically, for access by an operator, through an upper plastic cover plate 26 adhered to the top of the outer shell of the iontophoretic device 10. The switch 24 is electrically connected in the chamber 12 to the electronics package 15. The switch 24 may be selectively moved between a "0" (off) position, to either a "LO" (low current or lower rate of drug delivery) or "HI" (high current or higher rate of drug delivery) switch positions, to either turn the device 10 "off" so as to cease electrical operation, or to set the device for either high or low electric current rate operation which can remain in such a state on the patient, continuously if desired, for typically either 3 days or 7 days, respectively. Battery replacement, as needed, will repeat this service interval.

The function of the switch 24 in FIG. 1 with markings "0" (meaning off), "LO" and "HI" is as follows:

1) The "0" position keeps the device from functioning. It may also be used to schedule. an "off" interval after leaving one of the other drug delivery positions.
2) The "LO" treatment position infuses the drug at the lowest current level at a continuous, controlled rate. This position can be used for drugs with a narrow therapeutic index for low level infusion. Another use for this position could be a drug with a long half-life with a schedule of intermittent "0" positions to avoid an accumulation that might otherwise result in toxicity.
3) The "HI" treatment position of the switch 24 infuses the drug at a current level typically twice as high as the "LO" setting. This position may be used to maintain efficacy for drugs with a short half-life, such as peptides. Also, the "HI" position can be used for a bolus dose coming off the "LO" position, when therapeutically indicated.

For automatic operation, the manual controls discussed above are superceded by the biosensor developed data, to control current level and time of infusion as determined by the dosimetry system for exact quantitative infusion.

An LED test indicator 28 extends from the electronics package chamber 13 below the cover plate 26, through an appropriate opening in the cover plate, and is observable from the top of the iontophoretic patch 10 to confirm proper electrical operation of the system for the user. An additional switch 29, such as a membrane switch located inside the patch 10 below the cover plate 26, and operable by pressure on the flexible cover plate, (not shown) may be included to selectively connect the indicator 28 into and out of the electrical circuit, so as to minimize power drain when the indicator is not needed.

A bolus switch 52 is also provided for initiating and terminating bolus delivery of medicament in a manner subsequently described a replaceable biosensor 70 includes a pair of juxtaposed electrodes 72a, 72b with an electrically insulating membrane 74 interposed between the latter electrodes. An intervenor pad 76 is electrically connected to the biosensor and to a remote electrical source of high negative D.C. polarity for sample withdrawal of the desired analyte. The intervenor pad 76 provides a long tortuous path between the high negative voltage and the biosensor 70.

Figure 4:
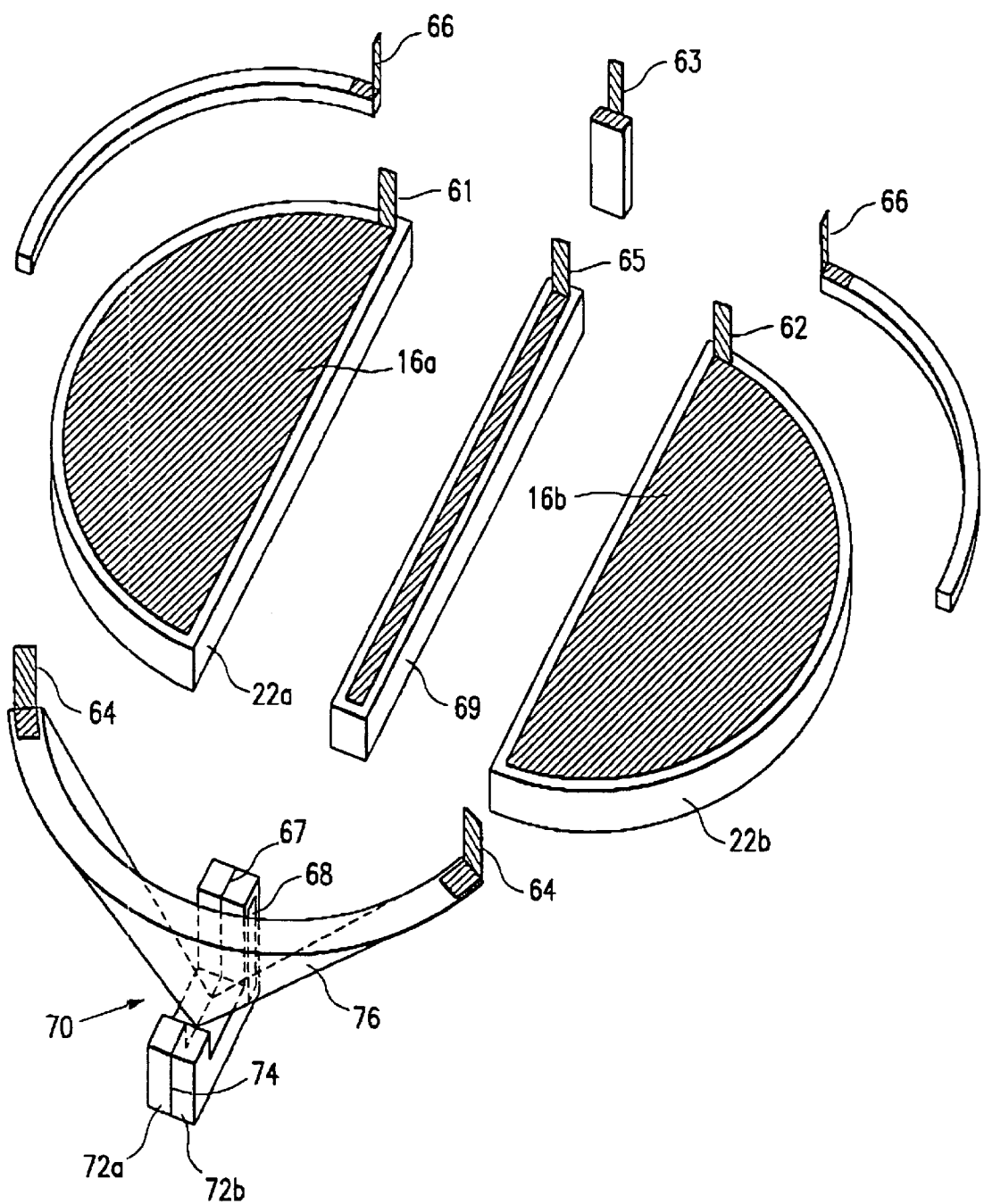
FIG. 4 is an exploded perspective view of a biosensor and fluid delivery device, constructed in accordance with the present invention.

Referring now more particularly to FIGS. 3A, 3B and 4 of the drawings, the electrodes 16a, 16b are located in the drug reservoirs 18a, 18b (FIGS. 2, 3A and 3B) and are A.C. driven for general drug delivery, as described in the aforementioned U.S. Pat. No. 5,224,927. For bolus insulin delivery, both electrodes 16a and 16b are shorted together in parallel and made negative in polarity. Ground return for bolus treatment is provided in peripheral outer thin pads with ground return terminals 66.

Figure 5:
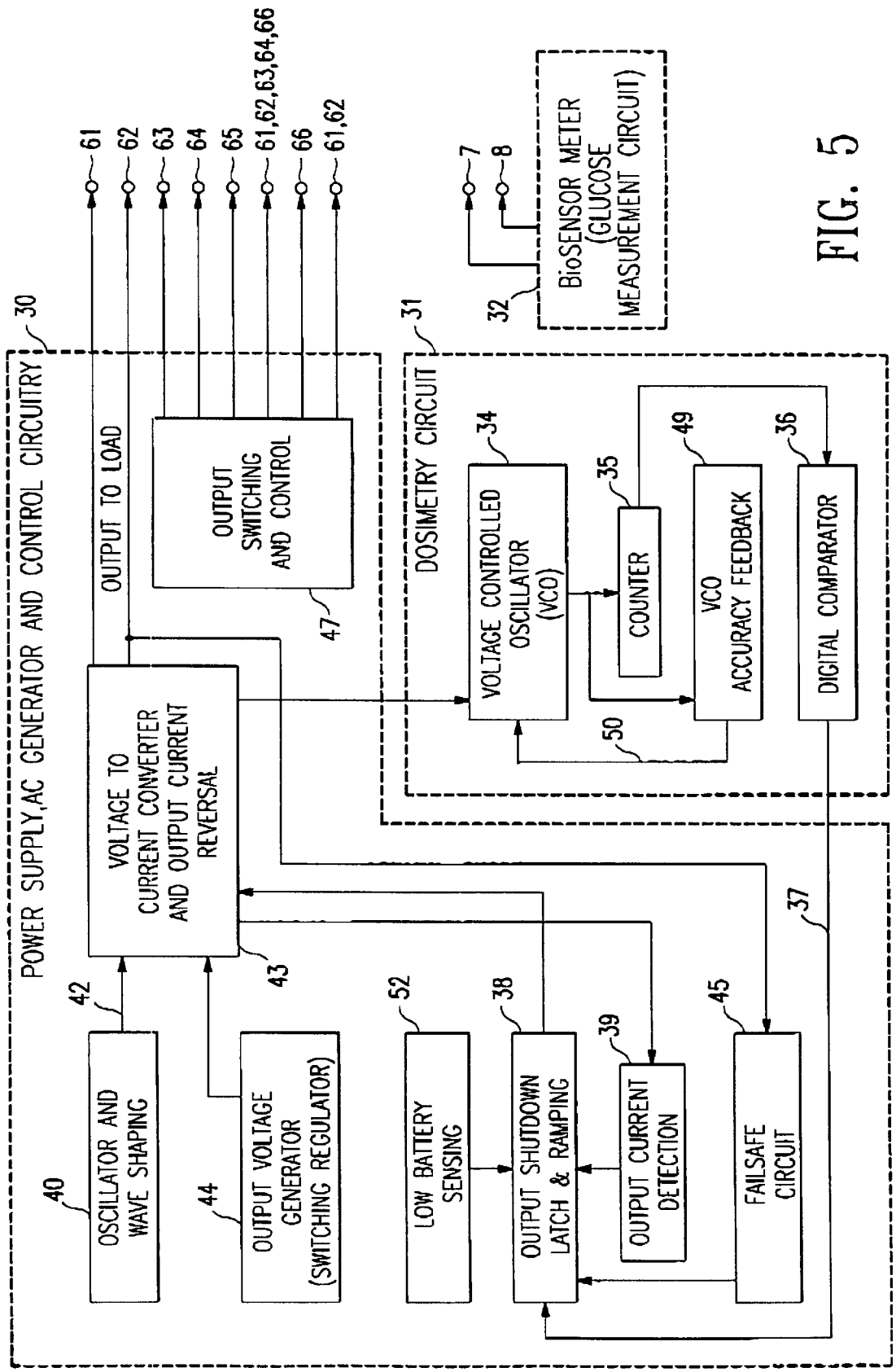
FIG. 5 is a block diagram of an electrical system for non-invasive analyte withdrawal, evaluation and therapeutic agent delivery in accordance with the present invention.

The iontophoretic delivery subsystem in the patch 10 is adapted to be automatically controlled by the dosimetry subsystem in FIG. 5.

The pH control pads 69 may be made either + or −. The electrode 65 is the ground return for pH control.

The high voltage electrodes 64 provide approximately 60 volts negative D.C. to the felt intervenor pad 76 which, in turn, provides a long tortuous path for electrical current to the replaceable sensor unit 30 which in turn, provided output at terminals 67, 68 in FIG. 5.

As previously indicated the sensor unit 70 includes a plurality of sensing and assay electrodes 72a, 72b with an appropriate membrane 74 therebetween. The structure of the sensor unit 70 is subsequently described in greater detail with reference to FIGS. 6 and 7 of the drawings.

Figure 6:
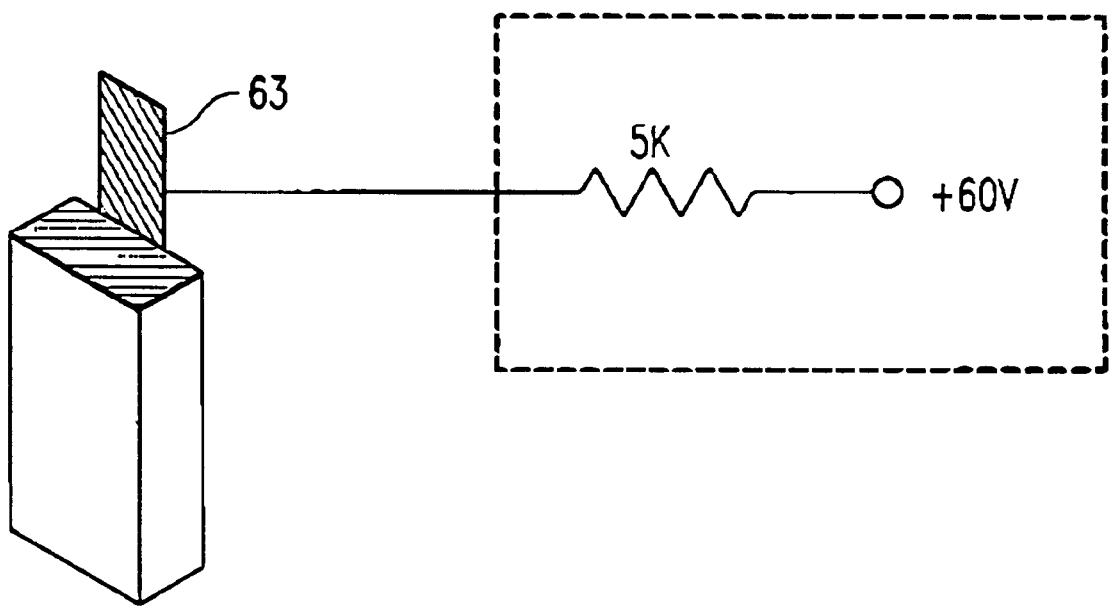
FIG. 6 is a combined electrical diagram and perspective view illustrating a portion of a biosensor and fluid delivery device, in accordance with the present invention.

The ground return 63 in FIG. 4 is directed through an appropriate isolation resistor, typically of 5 kilohms, to a remote source of positive high voltage (approximately +60 volts D.C.), as shown in FIG. 6.

Figure 7A:
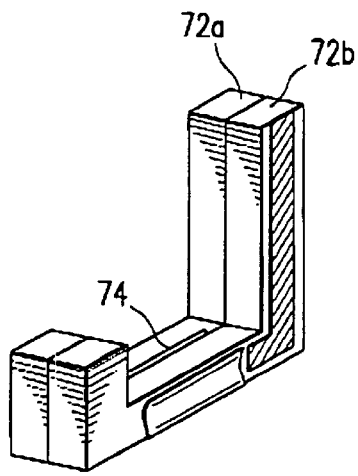
FIGS. 7a–7d are enlarged perspective views of biosensor electrodes and membrane construction, in accordance with the invention.
Figure 7B:
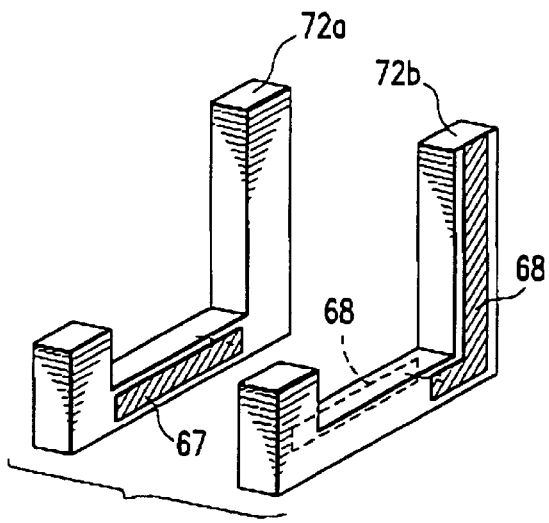
Figure 7C:
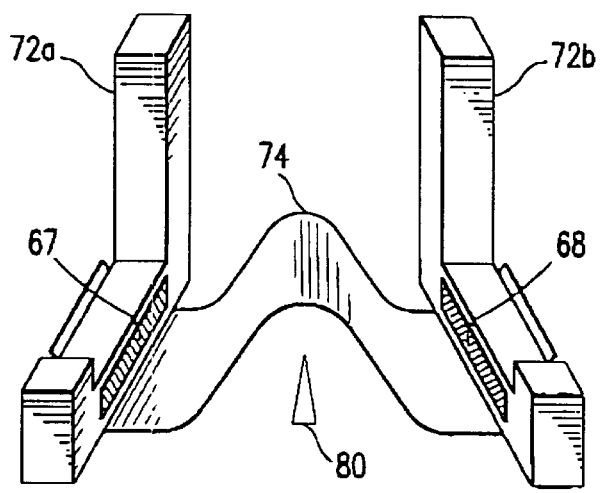
Figure 7D:
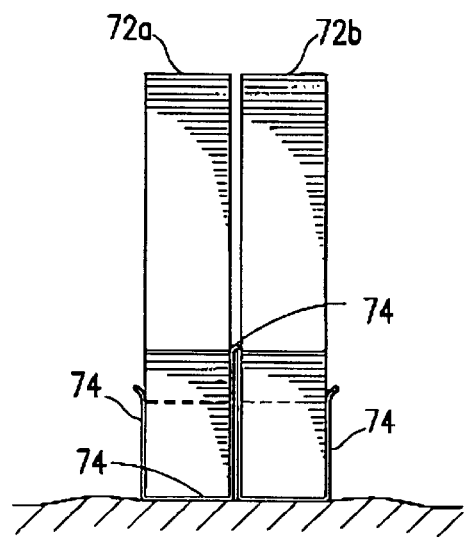

FIGS. 7a and 7d show the assembled biosensor 70 with electrodes 72a, 72b, fabricated of electrically insulating material, and a thin membrane 74 sandwiched between the electrically conducting electrode surfaces 68 and 69 located on confronting faces of a pair of electrode supports.

FIG. 7b shows the pair of electrodes 72a, 72b and supports their supports and electrode faces 68, 69 in disassembly to illustrate internal construction, while FIG. 7c shows the electrodes with the membrane 74, and a reference electrode 80, prior to final assembly to provide the structures shown in FIGS. 7a and 7b.

In a two electrode system as shown in FIG. 7, the electrodes can be composed of the following materials. For the reference electrode 80 (or counter electrode), it is desirable to have an inert but conductive material. In view of the fact that negative pole generated hydrogen is used as a reducing agent, it is imperative that the reference electrode 80 show maximum stability. A presently preferred choice for this reference electrode is material NASA-23 available from NASA. Its prime characteristic is that it is a hydrogen resistant alloy. Other commercially available choices or equivalents would be materials commonly identified commercially as A-286, 718, JBK-75 and Incoloy 903. The working electrode 67 would be composed of finely divided palladium (known as palladium black). Hydrogen readily permeates the palladium and in doing so has extended surface which adds to the current.

Another suitable structure would be for the enzymes to be coated on the palladium and the palladium to be backed by NASA-23 or its equivalent. The effect would be for the hydrogen reducing agent to directly reduce or oxidize the enzymes and for the hydrogen to permeate the palladium but be reflected back from the NASA-23 or its equivalent. This would maximize the oxidation effect and transfer of electron charge to the palladium electrode. The bi-layer dielecting membrane 74 (BLM) in between the electrodes can actually benefit from a choice of two materials i.e., cellulose and Nafion. These membranes may be coated with glucose dehydrogenase and NADH. The two plated electrode surfaces 67, 68 facing each other with dielectric membranes 74 in between provide capacitive coupling.

Figure 8:
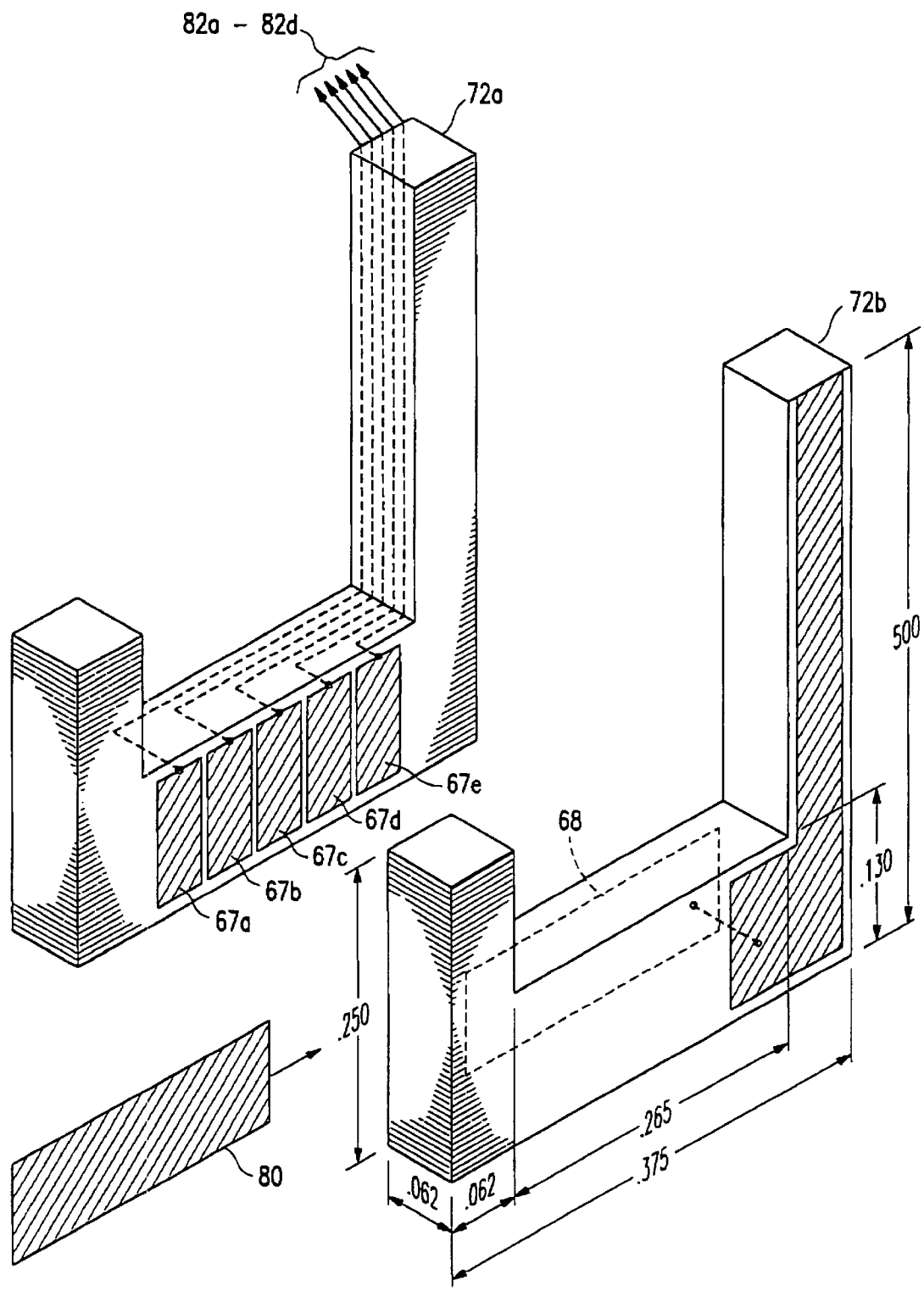
FIG. 8 is an enlarged, perspective view of another biosensor electrode construction, in accordance with the invention, and having multiple diagnostic capabilities.

FIG. 8 illustrates another example of electrode configuration with plural working electrodes 67a–67d and corresponding electrical outputs 82a–82d, respectively, to facilitate multiple diagnostic capabilities. The reference electrode 80 is surrounded by the membrane 74 (not shown in FIG. 8) and is positioned between the working and counter electrodes 67, 68.

Typical dimensions for the various electrodes and the support mounting structure are also provided in FIG. 8.

In accordance with the invention, a sensor can be provided which operates without enzymes. In this regard, for example, noble metals such as platinum can be substituted for glucose oxidase to catalyze the oxidation of glucose.

In the practice of the present invention, the limits of low voltage and current imposed on the prior art approaches, such as those described in U.S. Pat. Nos. 5,279,543 and 5,362,307 to prevent skin injury, are overcome through the aforedescribed unique electrical circuitry and long tunnel routing of applied voltage through the intervenor 76. In this regard, it is possible to apply 60 to 70 volts D.C. to the active negative electrode 64 and draw up to 3 milliamps with no injury. This resulted in current density of approximately 6.7 ma. per cm2 or approximately 30 times more current than the 0.22 ma. per cm2 of the aforedescribed prior art. In addition, the sampling was completed well within the necessary 10 minutes. Further refinement of the process permits allowed use of 60 volts producing a controlled sampling current of 1.5 ma. for complete user comfort, and that provided an analyte reading in approximately 15 seconds. The current density for this later model was 2.8 ma. per cm2 which was 13 times greater than the currents produced in the abovementioned prior art patents. A further experimental model calls for 6.2 ma. per cm2 or approximately 28 times more density than described in the aforementioned prior art patents and faster than the aforementioned 15 seconds. All of this is accomplished without skin injury.

Three of the primary features of the invention that make all of these desirable advantages feasible are described as follows:

In accordance with the invention, the aforedescribed features are accomplished, in part, by providing a long torturous path between the applied high voltage and the skin of the subject, i.e., via the intervenor 76. This path between the voltage source and the skin typically consists of a solvent or water wetted wool pad; see the pad 76 in FIGS. 2, 3A and 4. Since the injury is caused by sodium hydroxide (lye) migrating from the negative voltage source electrode 64, the wool (or composite) acts as a mechanical barrier to the rather large sodium hydroxide molecule to prevent injury within the maximum 10 minute treatment period.

In another embodiment of the invention, an alternative is provided to a tortuous felt pathway to prevent skin injury by preparing a thin felt intervenor pad (not shown) with a chemical pH that is opposite to the chemical pH of the drug delivery reservoirs 18a, 18b. For instance, for the short term analyte withdrawal by the sensor 70, a negative polarity connected to a thin intervenor felt quickly accumulates a large quantity of alkaline sodium hydroxide which would lead to a burn. However, if the pad is prepped with acidic hydrochloric acid controlled by novel pH circuitry, e.g. or in U.S. Pat. No. 5,224,927, this would neutralize any injury causing ions. Another approach is to use a pad that was previously coated with an acid or alkaline chemical to buffer the injurious chemical being generated at the electrode.

Since one aspect of the invention involves a diagnostic tool, accuracy and repeatability are paramount. To obtain accuracy and repeatability, a key requirement in the practice of the invention is that the current and time used to obtain the analyte sample be integrated and interdependent on each other so that the identical quantitative sampling is always obtained; i.e., to obtain consistent analyte sample size from one measurement to another. In this way, the substantial variabilities of skin resistance on an individual and between different individuals will always produce the identical amount of analyte which is withdrawn as a sample for subsequent analysis.

Another aspect that limits the use of higher currents is the patient pain involved. Usually, both electrical polarities are in direct contact with the skin through a felt or gel intervenor. As previously indicated, of the two polarities, the sensation at the positive electrode is typically far more painful to the patient. If therefore, direct contact of the positive electrode is removed from the skin, it allows a large increase in sampling current without the discomfort normally associated with such high electrical current, and still obtain the analyte, such as glucose, at the negative electrode.

To eliminate pain caused by the positive polarity at high currents, the following novel technology, in accordance with the invention, is provided. Previously used circuitry in iontophoresis used both polarities applied to the skin surface to "complete" or ground the circuit. In the practice of the present invention, the negative polarity is chosen to sample glucose and the positive electrode is no longer directly connected to the body as a ground return, but remains within the device housing 10 with its dropping resistor in FIG. 6 connected to the skin 11 (ground) to complete the circuit. This ground is essentially neutral. The negative polarity is in electrical contact with the skin 11 through the aforementioned wetted, long wool intervenor 76, and then through a wetted membrane 74 on the skin which acts as a collector for the analyte. Of course, for other applications these polarities could be reversed and, again, only a single polarity 2 would be in contact with the skin.

The present invention also provides a system to assay or measure the sample. A pair of electrodes 72a, 72b are provided facing each other with analyte selective enzyme coated on one electrode, e.g., the working electrode 67, or, alternatively, on the membrane 74 facing the working electrode. A bi-layer membrane (BLM) is inserted between these electrodes 67, 68 and serves the purpose of connecting directly to the skin 11 on one end while the other end is in contact with the long narrow intervenor 76 that is connected to the high voltage negative source at 64 (FIG. 4). When wetted with an electrolyte of pH 7.4, a continuous circuit is provided from this high voltage source to the skin (with felt pad 76 and membrane 74 in between). Thus, in accordance with the invention, a "sandwiched" bi-layer membrane 74 in between an enzyme coated electrode(s) 67, 68 or membrane 74 is provided as a mechanical structure to extract the analyte sample and convey it to any appropriate digital measurement subsystem 32 (FIG. 5).

To initially demonstrate the efficacy of the invention and its operating principles, a commercially available ExacTech® instrument was experimentally modified to be compatible with a prototype noninvasive means of analyte sampling of the present invention. This required that the ExacTech® test strip containing the enzymes and mediator be slit in half lengthwise. The chemically coated strip was then mounted with the two chemical surfaces facing each other and an electrically neutral nylon membrane was then inserted between these strips and provided an electrical and physical connection directly to the skin 11 on one end, with the other end in contact with the long narrow intervenor 76 that was connected to a 60 volt D.C. negative source.

The biosensor 70 circuit 32 is separate from the withdrawal circuitry 30, 31 in FIG. 5 and comes into play only after the analyte sample is withdrawn. The dosimetry circuit turns the device on for the predetermined setting of 15 ma./sec. to extract the analyte. Upon completion of this cycle, the readout in the form of the commercially available ExacTech® meter was activated and provided a reading on its digital display. Thus, we were able to run a series of tests confirming accuracy and repeatability of data against blood samples done in the intended manner of normal use for the ExacTech® unit.

Of course, in the commercial use of the noninvasive means of sampling of the present invention, there is no intention to use the ExacTech® sensing device as a detector. Any number of detection systems are available, including those in the public domain. The ExacTech® unit is primarily centered on its mediator system using ferrocene derivatives as an oxidant to effect transfer of electrons, and its description here is solely for the purpose of describing early experiments in the development of the present invention.

In accordance with the invention, electronically produced gases serving as mediator are generated at the high voltage negative terminal. These gases are created by the electrolysis action that takes place since the electrodes are immersed in a water solvent or electrolyte and connected to a source of voltage. The negative polarity, besides producing the necessary current to withdraw the analyte, also produces hydrogen gas at the negative pole which migrates towards the positive pole and thus passes through the membrane 74 and between the biosensor electrodes 68, 69. The hydrogen gas is a reduction agent and reduction cannot exist without oxidation. This oxidizes the immobilized enzymes on the electrodes/membrane and the captured glucose analyte. This also causes electron transfer to the electrodes that is proportionate to the concentration of analyte.

Hydrogen gas is an excellent redox species and is far superior to the "one shot" mediator of prior art devices, such as the well-known and commercially available ExacTech® device, because it comes from a renewable source. This process also produces the halogen chlorine which aids in oxidation formation.

In addition, in accordance with the invention, the high voltage source is dosimetry controlled and, therefore, not only quantitatively controls the analyte withdrawal but also controls the quantity of the aforementioned hydrogen/chlorine gas mediator which is generated.

This negative electrode generated hydrogen also serves other important functions. Since hydrogen has a special affinity for palladium and will permeate its surface, this may be used to advantage by providing a sensor electrode of palladium. Hydrogen interacts with the palladium to lower resistance. If the working electrode 67 is palladium and the second electrode 68 of the hydrogen resistive alloy NASA-23 or its equivalent, the resistance or work function between both electrodes is lowered. Because the NASA-23 or equivalent counter electrode 58 is impervious to the hydrogen gas, it serves as an excellent reference electrode relative to the palladium electrode 67.

Still other benefits accrue when hydrogen ions combine with the solvent water molecules to create hydronium ions. The hydronium ions are crucial to the cellular processes which lead to enzyme catalysis and membrane transport.

In accordance with the invention, very high potentials (over 1v.) are provided to cause the redox reaction. There is a two-step process, i.e., 1) a high voltage to cause the redox (generated by the reducing agent hydrogen), and 2) then revert to an extremely small voltage (under 1v.) to activate the transducer and readout system 32 (FIG. 5). This occurs almost instantaneously because the conventional time of 20–30 seconds to await the redox reaction has already taken place in much less time by the high voltage caused hydrogen that led to that event in much less time than any prior art device.

Accordingly, and in view of the foregoing, the process of the present invention includes application of a large negative voltage to a small area of the skin 11 to cause the electro-osmotic withdrawal of body fluids. This same high voltage has another attribute in that it generates hydrogen—the same hydrogen gas that will lead to the oxidation of the glucose enzyme(s) that separates out the glucose analyte from interferents. This causes the cycle of events that will result in electron transfer from the closely associated enzyme(s) coated electrodes 67, 68 to give a reading of glucose concentration. Moreover, the source for the hydrogen is unlimited and repeatable, therefore making the process available on demand without the physical presence of any consumable chemical mediators. Since the enzymes are reusable, the economy and simplicity of operation of such a device provides clear advantages to the patient.

To reuse the device 10 and obtain new glucose readings and repeat the events leading to insulin infusion, the second half of the one cycle long signal reverses polarity and returns the system to neutral. Alternatively, the patient can wait several minutes for the chemicals of the just concluded test to dissipate.

Another feature of the invention that improves the minute sampling taken through the unbroken skin 11 is the use of the amplification or regeneration capability of certain chemical combinations. If the electrodes 67, 68 are coated with coupled enzymes, such as glucose oxidase or glucose dehydrogenase in the presence of cofactors NAD/NADH and NADPH or NADH, then the extremely minute analyte coming through the skin is "ping ponged" between competitive enzymes and therefore multiplied. Another benefit of this is improved separation between the target glucose and interferents.

Hence, various aspects of the present invention facilitate noninvasively withdrawing body fluid and provide novel sensor technology to create a mediator and to control the quantity of this mediator for accurately determining analyte concentration for diagnostic purposes. These inventions can be used separately or in combination, and both use common components that have multiple functions. This dual capability of noninvasive sampling and controlling the target inorganic or organic substance is a linchpin to the control and operation of a therapeutic drug delivery unit such as that described in U.S. Pat. No. 5,224,927 by the same inventor, Robert Tapper, as the present invention. This "closed loop" arrangement provides for self-regulated insulin infusion controlled by the monitored glucose reading using the biosensor 70 described above. The entire device can fit into an externally worn, topically applied "patch", as illustrated in FIG. 1.

Another important feature referred to in U.S. Pat. No. 5,224,927 is the ability of this device to adjust the pH of the drug delivery reservoirs and/or the biosensor skin contact membrane 74 (known as BLM or s-BLM). The pH adjustment range is 4 to 8 and can aid in permeability for both infusion of drug or increasing withdrawal of analyte. For instance, in view of the nonconductive wetted collection bi-layer membrane 74 (BLM) in contact with the skin 11, and in view of the poorly conductive insulin in the drug delivery chambers 18a, 18b, optimal performance would take place if the solution were adjusted to the appropriate pH. An important function of the s-BLM is that it be used as a pH probe for pH measurement. The resulting pH data is then the basis for a pH control circuit to adjust pH as needed.

The aforedescribed system of the present invention relates in particular, and by way of example, to the needs of a diabetic. Another need of the diabetic is that they be given a "bolus" shot of insulin at mealtime. A bolus shot requires the infusion of a large dose of insulin compared to their baseline maintenance level. The system described in U.S. Pat. No. 5,224,927 is readily adapted to meet this demand for an extra large dose in the following manner.

By activating the designated electrical bolus switch 52, both drug delivery reservoirs 18a, 18b of the patch 10 are made active simultaneously instead of their normal operating mode of sequential drug delivery (due to the very slow A.C. operating signal). Since the bolus switch 52 causes both reservoirs 18a, 18b to deliver insulin simultaneously by giving them the identical negative polarity, the dosage is thereby doubled over baseline.

As previously indicated, the positive polarity stays within the housing of the electronic patch 10 and is connected to the skin 11 through a dropping resistor; see FIG. 6. The skin 11 or ground is relatively neutral at this point. This feature lifts the positive polarity off the skin 11, thereby eliminating the more painful and non-contributing positive polarity from skin contact. This, in turn, allows the patient to at least double the electrical current setting, thereby again doubling dosage, for a total of four times over maintenance level for short term delivery. For this short term delivery a D.C. signal is used. Because it is a D.C. signal, skin injury could be expected unless corrective action were taken. Previously, the use of the pH control circuit served the singular purpose of optimizing permeability and therefore delivery, by making the solvent compatible with the drug of choice and its polarity. In accordance with the present invention, pH control is also used to prevent skin injury when using D.C. for the short term. For instance, in the example cited above, the negative polarity was used to drive insulin from both reservoirs 18a, 18b. The injurious sodium hydroxide generated at the negative pole must then be offset. This can be done by pretreating with the positive polarity, thereby building an acidic reserve pH of approximately 4 (by way of example) in the drug delivery reservoirs. Drug delivery is then activated with a negative polarity driving the pretreatment pH up toward the alkaline state. Before the reservoirs reach pH 8, the delivery signal must be stopped for another short dosage of pH 4 caused by the positive polarity. Thus, injury is prevented by avoiding extremes of pH as measured by the s-BLM probe.

Figure 9:
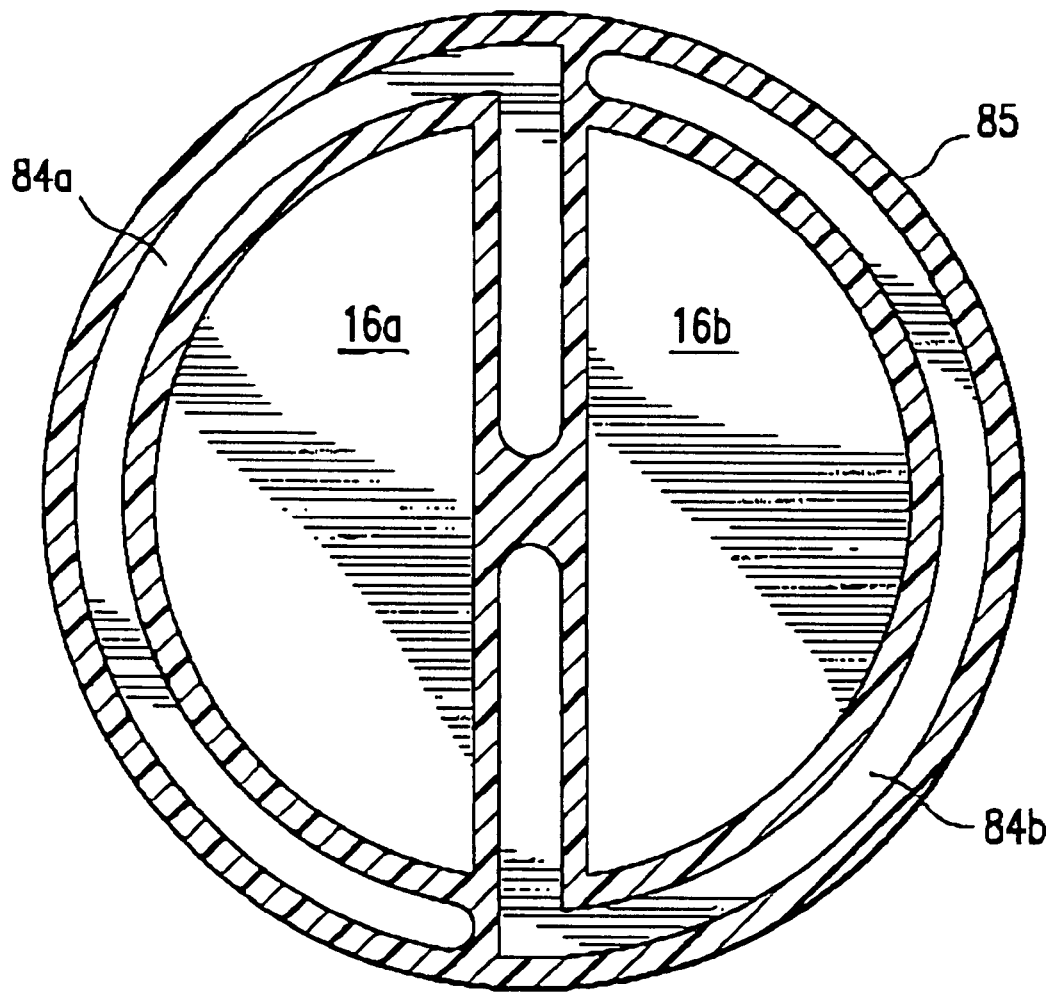
FIG. 9 is a cross-sectional view of another embodiment of the invention, illustrating new and improved electrode construction.

The invention also includes a unique electrode system that allows current to be elevated at least 200% over present levels. The large drug delivery electrodes 16a, 16b are shown in FIG. 9. Another pair of ancillary electrodes 84a, 84b have been added on the outside perimeter of the electrodes 16a, 16b that also cross between and are insulated from the electrodes. These outer ancillary electrodes 84a, 84b are typically driven at a frequency of approximately one cycle per minute. This is the second harmonic of the basic drug delivery generator with a frequency approximately one cycle every two minutes. It has been discovered that the use of the electrodes 84a, 84b to deliver sodium salicylate is able to mask the pain sensation of the drug delivery electrodes 16a, 16b so as to facilitate vastly increasing the electrical current levels.

In accordance with the invention, it has been discovered that sodium salicylate delivery also minimizes skin injury.

Furthermore, the dual frequency process also is effective in accommodating the transport times of different size molecules and removing clutter.

Another important need for a bolus dose is in the field of anesthesia since it is desirable for quick action to alleviate pain. The same procedure for elevated infusion-applies as above with pH control to avoid injury, but may require switching polarities since many analgesics are positive. In this regard, and referring again to FIG. 9, a D.C. signal is used with novel circuitry to obtain greatly elevated drug delivery levels without skin injury or pain. To lessen pain and skin injury from the positive reservoirs containing drug delivery electrodes 16a, 16b, we connect these electrodes through a dropping resistor of perhaps 5 k to 20 k instead of connecting directly to the positive terminal of the voltage supply. This causes a large drop across the resistor and makes the electrode relatively less positive than the source voltage. Electrical current still flows because the negative polarity is directly connected to the skin 11 through the wetted pad 74. The result is a lifting and isolation of the pain-causing high positive voltage relative to the skin. This allows increased levels of electrical current and therefore faster therapy. Diminished positive voltage at the skin also decreases the potential for irritation from this contact. Importantly, it has been discovered that adding sodium salicylate to the negative pad also diminishes skin injury which would normally be a concern with a D.C. device.

The aforedescribed artificial pancreas of the present invention has obvious advantages over present day invasive systems that include expensive and risky implants.

It is to be understood that the noninvasive biosensor described above used glucose as the target analyte only as an example and not by way of limitation. For instance, there are over 250 different dehydrogenases and several thousand enzymes. Besides glucose analysis, important diagnostic applications could include urea, creatinine, lactate, cholesterol, aspirin and paracetamol among others. Also, noninvasive sample analysis may be made of body fluids to compare to normal levels or to track administered drug levels.

Since the present invention focuses on a means of determining the concentration of chemical or body fluid components to assess a condition, another important application is suggested. During iontophoretic drug delivery, it has long been an enigma as to what part of the reservoir drug has been infused. In this regard, the same means of determining concentration with the biosensor 70 described above may be applied to assessing the drug remnant in a drug infusing device, therefore assuring the user of adequate drug availability, etc. This occurs because a decrease of concentration indicates percutaneous absorption into the body of the solute or drug. This information may also be important to the investigator during the testing of a new drug, for quantitative analysis of drug related to an effect. The present invention thus nominally replicates the extremely expensive HPLC lab instrument at a fraction of the cost.

Still another important application, in accordance with the invention, comes about as a result of this ability to assess drug concentration in an iontophoretic drug delivery reservoir. It has always been a problem to have an adequate supply of drug available in the drug reservoir for long term, continuous delivery. It is not practical to make an overly large patch because it must be worn and would meet patient objection. Also, the literature places concentration restrictions on iontophoretic drug delivery to 2% solutions, claiming reduced flow above this point because of ionic clutter. In accordance with the present invention, a novel way of eliminating this problem and allowing delivery over time with a relatively small patch is to provide a reserve reservoir that contains a concentrate of the desired drug in aqueous solution. The concentrate is considerably over 2%—perhaps 20 or 50%. Upon receiving information from the drug delivery reservoir that the concentration is less than the initial filling of 2%, the biosensor 70 triggers the reserve reservoir to release enough of the concentrate to make up the difference that was infused. In this manner, the drug reservoir is continuously replenished.

The structure of the reserve reservoir (not shown) is a separate compartment for the concentrate with a membrane covered opening. The membrane has a voltage across it with selective polarities to act as a valve to open or shut off the flow of concentrate as needed. This action may be enhanced with an ion exchange membrane. The solvent is replenished automatically by virtue of the fact that an A.C. signal is used. This causes the hydrogen and hydroxide ions to migrate together to form water.

Various other embellishments known in the art can be practiced in accordance with this invention. They include immobilization of the enzyme biocomponent and restriction of the flow of analyte diffusion. The best biosensor design is to build a "direct" device with biocomponents immobilized directly on the transducer. Other characteristics of construction include the close proximity of the biological and physicochemical components to each other to improve efficiency.

The present invention also provides in combination with the aforedescribed sample withdrawal and assay, and in response to electrical input from the assay subsystem, a new and improved method and apparatus for applying electrical energy topically to a suitable surface of a biological subject, such as the skin of a human body, particularly for the long term administration of medicaments and the like or for other electrotherapeutic treatment, and by which the aforementioned deficiencies and undesired side effects are greatly minimized and may be eliminated. Moreover, the system of the present invention is relatively inexpensive to manufacture, can be physically packaged in a completely self-contained, relatively simple and compact configuration, trouble free and reliable in use, is capable of higher drug administration rates and drug concentrations, can deliver multiple drugs simultaneously in a simple manner, can control pH at the delivery site, is capable of delivering large and/or heavy molecule drugs, is a more effective bactericidal, and is arranged to be safely, simply and reliably operated for self-treatment by an average person in normal home use, even for extended periods of several days at a time. Furthermore, it is contemplated in the practice of the invention that electrical impedance at the administration site on the patient can be substantially reduced to vastly improve permeability and penetration and thereby further enhance medicament delivery.

In this regard, the present invention is directed to a new and improved system for analyte sample withdrawal and subsequent iontophoretic drug administration, in response to an assay measurement signal, which includes conducting direct electrical current through the skin of a body, and periodically reversing the electrical current and conducting the electrical current through the skin in the opposite direction, to effectively deliver very low frequency A.C. current, substantially in the critical range of approximately 0.0027 Hz to 10 Hz. It has been discovered (see U.S. Pat. No. 5,224,927) that, within this substantially critical frequency window between approximately six minutes per full cycle and approximately ten cycles per second, a dramatic cancellation of skin damaging ions takes place. At frequencies higher than approximately 10 Hz, no substantial effective delivery takes place. At frequencies lower than approximately 0.0027 Hz, the risk of skin injury increases substantially.

As previously indicated, it is well known that the positive iontophoretic electrode, in addition to its primary function of driving like polarity ionic substances into the skin of a subject, unfortunately produces skin damaging hydrochloric acid as well. Likewise, the negative iontophoretic electrode, in addition to its primary function of driving like polarity ionic substances into the skin, unfortunately also produces skin damaging sodium hydroxide. However, within the aforestated frequency range of the present invention, either driving polarity delivers the desired ionic therapeutic substances, but also cancels the undesired skin damaging ions with the reverse portion of the electrical cycle. The reason for neutralization of the harsh injury producing chemicals, i.e., hydrochloric acid and sodium hydroxide, is that both of these chemicals require a finite period of time on the skin to cause damage. Hence, these damaging chemicals are made to cancel each other before damage takes place, by critical frequency selection of the A.C. driving signal. Therefore, optimization of a long sought therapeutic device with reduced side effects has been achieved.

In this regard, electronic circuitry is provided to automatically impose the reversal of electrical current at regularly repeating intervals of time, in accordance with the aforedescribed substantially critical frequency range, and the system can be adjusted to conduct the iontophoretic treatment at any desired level of electrical current.

As previously indicated, the present invention provides a method and apparatus for electrical dosimetry control for the electro-osmotic withdrawal of fluids from a biological subject to obtain an analyte sample dosage being determined by the product of time and electrical current, wherein electrical current magnitude and time are fixed to automatically assure consistent sample withdrawal from one procedure to another and thereby maintain calibration for accuracy.

In accordance with the invention, the same dosimetry control subsystem can be switched to control the dosimetry of the slow A.C. signal driven iontophoretic administration subsystem, independently of whether or not the sample withdrawal and biosensor assay subsystems are also employed.

Hence, the present invention includes, in an electro-osmotic withdrawal system, a subsystem for electrical dosimetry measurement and control, wherein the product of administered electrical current and time for total dosage is maintained constant, while either variable, time or electrical current magnitude, may be changing. A system which can be adapted for implementing such measurement and control is described in U.S. Pat. No. 4,822,334 issued Apr. 18, 1989, inventor Robert Tapper (the same inventor as the present invention) and all of the disclosure of this patent is specifically incorporated by reference in this specification as if set out completely herein. The disclosure of this patent is directed to an iontophoresis environment, but, in accordance with the present invention, the control system is adapted for electro-osmotic sample withdrawal rather than iontophoretic fluid delivery.

Such a system, by way of example and not necessarily by way of limitation, includes means for applying electrical current to a load, such as a human patient, over time, together with means for automatically varying the magnitude of the current and/or time to ensure consistent sample size withdrawal. The system includes means for establishing the magnitude of the desired total withdrawn sample size dosage in terms of delivered time-current product and means for sensing the magnitude of the electrical current and converting that magnitude to a voltage for varying the frequency of a voltage controlled oscillator as a function of the electrical current magnitude. Means are also provided for measuring and accumulating the electrical output of the oscillator over time, in a suitable counting device, as an indication of the actually delivered time-current product. In addition, means are provided for comparing the delivered time-current product registered in the counter, as a running measure of electro-osmotic sample withdrawal during the administration procedure, with the desired total dosage previously established, so that the application of electrical current will be automatically terminated when the time-current product actually administered equals the desired total dosage, i.e., the size of the sample for subsequent assay.

In this way, desired sample withdrawal dosage is consistently and reliably delivered with great precision even though the electrical current may be varied during the sample withdrawal.

Referring now to FIG. 5 of the drawings, there is shown in detail a system for sample withdrawal and dosimetry control including a power supply, A.C. generator and control circuitry subsystem 30 and a dosimetry circuitry subsystem 31, as well as an output sensor and readout subsystem 32, shown by way of example as suitable for glucose measurement.

The electro-osmosis electrical current is sensed and converted to an appropriate voltage which is directed to a suitable voltage controlled oscillator (VCO) 34. In FIG. 5 the oscillator 34 generates output pulses whose frequency is proportional to the magnitude of the load current, and this electrical pulse output is directed to a counter 35 which essentially integrates the applied load current over time, via the counting of oscillator output pulses, to obtain an electrical current-time product providing a running measure of dosage actually withdrawn as a sample from the biological subject.

The state of the counter 35, i.e., the actually withdrawn sample dosage, is directed to a digital comparator where it is compared with the selected total dosage desired and, when the running measure of dosage indicated by the counter matches the total dosage selected, the sample withdrawal process is terminated by an appropriate output from the digital comparator. In this way, any variations in current and/or time during the sample withdrawal procedure will still provide a consistently reliable total dosage from one procedure to the next and, therefore, the parameters of time and electrical current can vary from subject to subject and from time to time with the same subject, without interfering with the precise total sample dosage withdrawn from the patient over the course of the procedure.

The sample withdrawal current is converted to a voltage which establishes the frequency of oscillation of the oscillator 34. The counter 35 accumulates the electrical output of the oscillator 34 over time, as an indication of the actually delivered time-electrical current product representing a running measure of dosage during the sample withdrawal procedure.

The electrical state of the counter 35 is then directed as input to the digital comparator 36 and, when the state of the counter 35 equals the desired total dosage to be withdrawn, represented by a predetermined dose already set in the digital comparator, an electrical output is generated from the comparator. This output is directed, over line 32, to the subsystem 38 to terminate the sample withdrawal procedure once the desired total dosage has been electro-osmotically withdrawn from the patient. Consequently, the desired total dosage is consistently and reliably withdrawn from the patient, with great precision, from one administration procedure to the next. This precise repeatability occurs even though the electrical current or time may vary substantially during the withdrawal procedure.

The subsystem 30 also includes an oscillator and wave shaping unit 40 directing output over line 42 to a unit 43 for voltage to current conversion and output current reversal, which is under the control of input from an output voltage generator (switching regulator) unit 44 and the output shutdown latch and ramping unit 38 via an output current detection unit 39. The unit 43, in turn, directs sample withdrawal current output to the patient (load) at a pair of output pins 61, 62 which are also used to control subsequent iontophoretic delivery in response to sample assay.

The unit 43 also provides output to the VCO 34 in the dosimetry subsystem 31 and to a suitable failsafe circuit which, in turn, has an output directed shutdown unit 38.

An electrical output switching and control unit 47 provides a (neutral) ground return for the sensor 70 at pin 63, the 60 volt negative output to withdraw a sample of analyte at pin 64, a ground return for pH control at pin 65, and a ground return for bolus delivery treatment at pin 66.

The control unit 47 also provides an output (labeled 61, 62, 63, 64, 66 in FIG. 5) to the target for pH control, as well as an output (labeled 61, 62 in FIG. 5) providing high electrical current for bolus treatment (which also serves as a reservoir for general drug delivery).

The pins 67, 68 are connected to the sensor output for the meter and associated circuitry of subsystem 32.

A VCO accuracy feedback unit 49 also receives the output from the VCO 34 which has been provided to the counter 35 and the unit 49 provides control input over line 50 to the VCO.

The digital comparator unit 36 provides input over line 37 to the unit 38 which, as previously indicated, provides input to the unit 43.

A low battery sensing unit 52 also provides input to the shutdown unit 38.

The aforementioned pin numbers 61, 62, 63, 64, 65, 66, 67 and 68 correspond to the labeling of electrical connections for the sample withdrawal, biosensor, assay and iontophoretic administration patch 10 shown in FIGS. 2–4 of the drawings.

It will be apparent that the various electrical subsystems indicated in FIG. 5 of the drawings can be implemented readily by those of ordinary skill in the art without the exercise of inventive skill. In this regard, Appendices A and B, attached to the specification and specifically incorporated herein, illustrated, by way of example, presently preferred embodiments of electrical circuitry suitable for implementing the primary subsystem schematically depicted in block diagram format in FIG. 5 of the drawings, for practice of the invention.

Hence, the present invention satisfies a long existing need in the art for painless, accurate, non-invasive analyte withdrawal and analysis and subsequent controlled delivery of therapeutic agents in response to such analysis. The present invention clearly fulfills these needs.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. In an electronic control system for electro-osmotic withdrawal of fluid samples from a biological subject, the combination comprising:

means for conveying a sample withdrawing electrical current to the skin of a biological subject;

means for varying the time period over which said electrical current is supplied to the biological subject in accordance with the desired sample size to be extracted from the biological subject; and means for terminating said electrical current applied to the biological subject when said electrical current-time product equals the desired total withdrawal sample size.

2. A combination as set forth in claim 1, wherein the magnitude of said electrical current is maintained constant during the time period that said sample is being withdrawn from the biological subject.

3. A combination as set forth in either of claims 1 or 2, wherein said means for conveying electrical current includes a source of high voltage.

4. A combination as set forth in claim 3, wherein said high voltage exceeds 15 volts.

5. A combination as set forth in claim 3, wherein said high voltage is of the order of magnitude of 60 volts.

6. A combination as set forth in any of claims 3–5 wherein said time period is substantially less than ten minutes.

7. A combination as set forth in any of claims 1–5, wherein said time period is approximately fifteen seconds.

8. A combination as set forth in any of claims 1–5, wherein said time period is substantially less than fifteen seconds.

9. An electronic process for controlling electro-osmotic withdrawal of fluid samples by electrical current applied over time to a biological subject, comprising the steps of:
establishing a total sample size to be withdrawn, in the form of an electrical current-time product, from the biological subject; and
automatically varying the time period over which said electrical current is applied by accumulating the electrical current-time product until termination at the selected withdrawal sample volume.

10. A process as set forth in claim 9, wherein the magnitude of said electrical current is maintained constant during the time period that said sample is being withdrawn from the biological subject.

11. A process as set forth in either of claims 9 or 10 wherein said time period is substantially less than ten minutes.

12. A process as set forth in either of claims 9 or 10, wherein said time period is substantially less than one minute.

13. A process as set forth in either of claims 9 or 10, wherein said time period is approximately fifteen seconds.

14. A process as set forth in either of claims 9 or 10, wherein said time period is substantially less than fifteen seconds.

15. A process as set forth in either of claims 9 or 10, wherein the electrical current is provided by a source of high voltage.

16. A process as set forth in either of claims 9 or 10, wherein said high voltage exceeds 15 volts.

17. A process as set forth in either of claims 9 or 10, wherein said high voltage is of the order of magnitude of 60 volts.

18. In an electronic control system for electro-osmotic withdrawal of fluid samples from a biological subject, the combination comprising:
means for applying a predetermined electrical current to a biological subject over time;
sample volume determining means for establishing the magnitude of the desired total sample volume to be withdrawn from the biological subject, in terms of electrical current-time product;
means for sensing the magnitude of said electrical current and for converting said magnitude to an electrical signal;
means for measuring said electrical signal over time as an indication of the actual electrical current-time product;
means for comparing said actual electrical current-time product with said desired total sample volume to be withdrawn; and
means for terminating said electrical current when said electrical current-time product equals said desired total sample volume to be withdrawn as established by said determining means.

19. A combination as set forth in claim 18, wherein the magnitude of said electrical current is maintained constant during the time period said sample is being withdrawn from the biological subject.

20. A combination as set forth in either of claims 18 or 19, wherein said means for delivering electrical current includes a source of high voltage.

21. A combination as set forth in claim 19, wherein a high voltage of the order of magnitude of 60 volts.

22. A combination as set forth in any claims 1, 2, 18, 19 or 21, wherein said sample is withdrawn from the biological subject and said sample is an analyte for subsequent evaluation.

23. A combination as set forth in claim 22, wherein said high voltage exceeds 15 volts.

24. A combination as set forth in claim 22, wherein said high voltage is of the order of magnitude of 60 volts.

25. In an electronic control system for electro-osmotic withdrawal of fluid samples from a biological subject, the combination comprising:
means for conveying a sample withdrawing electrical current to the skin of a biological subject;
means for determining the magnitude of said electrical current;
means for controlling the time period over which said electrical current is supplied to the biological subject;
control means for automatically determining the sample size to be extracted from the biological subject;
means for electrically measuring the actual sample quantity withdrawn from the biological subject as a function of said electrical current and time; and
means for terminating said electrical current applied to the biological subject when said electrical current-time product equals the desired total withdrawal sample size as established by said control means.

26. A combination as set forth in claim 25, wherein the magnitude of said electrical current is maintained constant during the time period said sample is being withdrawn from the biological subject.

27. A combination as set forth in claims 25 or 26, wherein said time period is substantially less than ten minutes.

28. A combination as set forth in either of claims 25 or 26, wherein said means for delivering electrical current includes a source of high voltage.

29. A combination as set forth in any of claims 25, 26 or 27, wherein said time period is approximately fifteen seconds.

30. A combination as set forth in any of claims 25, 26 or 27, wherein said time period is substantially less than fifteen seconds.

31. An electronic process for controlling electro-osmotic withdrawal of fluid samples by electrical current applied over time to a biological subject, comprising the steps of:
selecting a total sample size to be withdrawn, in the form of an electrical current-time product, from the biological subject;
determining the magnitude of said electrical current;

measuring said electrical current applied to the biological subject and automatically varying the time period over which said electrical current is applied by accumulating the electrical current-time product until termination at the selected withdrawal sample volume.

32. A process as set forth in claim 31, wherein the magnitude of said electrical current is maintained constant during the time period said sample is being withdrawn from the biological subject.

33. A process as set forth in either claims 31 or 33 wherein said time period is substantially less than ten minutes.

34. A process as set forth in either of claims 31 or 32, wherein said time period is substantially less than one minute.

35. A process as set forth in either of claims 31 or 32, wherein said time period is approximately fifteen seconds.

36. A process as set forth in either of claims 31 or 32, wherein said time period is substantially less than fifteen seconds.

37. A process as set forth in either of claims 31 or 32, wherein the electrical current is provided by a source of high voltage.

38. A process as set forth in either of claims 31 or 32, wherein said high voltage exceeds 15 volts.

39. A process as set forth in either of claims 31 or 32, wherein said high voltage is of the order of magnitude of 60 volts.

40. A process as set forth in any claims 9, 10, 6, 11, 12, 13–17, 31–39, wherein the system withdraws a sample which is from the biological subject and which is an analyte for subsequent evaluation.

41. In an electronic control system for electro-osmotic withdrawal of fluid samples from a biological subject, the combination comprising:
   means for applying a predetermined electrical current to a biological subject over time;
   sample volume determining means for establishing the magnitude of the desired total sample volume to be withdrawn from the biological subject, in terms of electrical current-time product;
   means for sensing the magnitude of said electrical current and for converting said magnitude to an electrical signal;
   oscillator means responsive to said electrical signal for varying the frequency of oscillation as a function of said magnitude of said electrical current;
   means for measuring and accumulating the electrical output of said oscillator over time as an indication of the actual electrical current-time product;
   means for comparing said actual electrical current-time product with said desired total sample volume to be withdrawn; and
   means for terminating said electrical current when said electrical current-time product equals said desired total sample volume to be withdrawn as established by said determining means.

42. A combination as set forth in claim 41, wherein the magnitude of said electrical current is maintained constant during the time period said sample is being withdrawn from the biological subject.

* * * * *